US012788481B2

(12) United States Patent
Yang et al.

(10) Patent No.: US 12,788,481 B2
(45) Date of Patent: Nov. 10, 2026

(54) INTERATRIAL MULTI-CUSPID VALVULAR SHUNT

(71) Applicant: Medtronic, Inc., Minneapolis, MN (US)

(72) Inventors: Zhongping C. Yang, Woodbury, MN (US); Thomas A. Anderson, New Hope, MN (US); Lars M. Mattison, Blaine, MN (US); Nicolas Coulombe, Anjou (CA); Randal C. Schulhauser, Phoenix, AZ (US); Robert C. Kowal, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 1115 days.

(21) Appl. No.: 17/664,824

(22) Filed: May 24, 2022

(65) Prior Publication Data

US 2022/0370120 A1 Nov. 24, 2022

Related U.S. Application Data

(60) Provisional application No. 63/192,218, filed on May 24, 2021.

(51) Int. Cl.
*A61B 18/18* (2006.01)
*A61B 17/00* (2006.01)
(Continued)

(52) U.S. Cl.
CPC .... *A61B 18/1492* (2013.01); *A61B 17/00234* (2013.01); *A61B 2017/00592* (2013.01);
(Continued)

(58) Field of Classification Search
CPC ...... A61B 17/00234; A61B 17/320725; A61B 17/3209; A61B 18/042; A61B 18/1492; A61B 2017/00592; A61B 2018/00196; A61B 2018/00202; A61B 2018/00214; A61B 2018/00261; A61B 2018/00351; A61B 2018/00357; A61B 2018/00577;
(Continued)

(56) References Cited

U.S. PATENT DOCUMENTS 5,196,024 A 3/1993 Barath
5,697,944 A 12/1997 Lary
(Continued)

FOREIGN PATENT DOCUMENTS

WO 2019177769 A1 9/2019
WO 2021011502 A1 1/2021

OTHER PUBLICATIONS

International Search Report and Written Opinion of International Application No. PCT/US2022/030768 dated Aug. 25, 2022, 13 pp.
(Continued)

*Primary Examiner* — Michael F Peffley
*Assistant Examiner* — Amanda L Zink
(74) *Attorney, Agent, or Firm* — Shumaker & Sieffert, P.A.

(57) ABSTRACT

A method includes cutting a septal wall between a right atrium and left atrium of a heart of a patient to form a multi-cuspid valvular shunt, and ablating septal wall tissue of at least a portion of the multi-cuspid valvular shunt to cause the ablated portion of the multi-cuspid valvular shunt to be biostable.

20 Claims, 10 Drawing Sheets

(51) Int. Cl.
*A61B 18/14* (2006.01)
*A61B 18/00* (2006.01)

(52) U.S. Cl.
CPC ............... *A61B 2018/00351* (2013.01); *A61B 2018/00577* (2013.01)

(58) Field of Classification Search
CPC .......... A61B 2018/00601; A61B 2018/00994; A61B 2018/0212; A61B 2018/1415; A61B 2018/1861
See application file for complete search history.

(56) References Cited

U.S. PATENT DOCUMENTS

| | | | | |
|---|---|---|---|---|
| 6,632,231 | B2 | 10/2003 | Radisch, Jr. | |
| 6,951,566 | B2 | 10/2005 | Lary | |
| 10,143,838 | B2 | 12/2018 | Grubac et al. | |
| 10,292,690 | B2 | 5/2019 | Celermajer et al. | |
| 10,842,556 | B1 * | 11/2020 | Tandri | A61B 18/1492 |
| 10,898,707 | B2 | 1/2021 | Eggen et al. | |
| 11,883,061 | B2 | 1/2024 | Gunderson et al. | |
| 2006/0111736 | A1 | 5/2006 | Kelley | |
| 2012/0191111 | A1 | 7/2012 | Aggerholm et al. | |
| 2014/0142564 | A1 * | 5/2014 | Werneth | A61B 18/1492 606/41 |
| 2015/0182282 | A1 * | 7/2015 | Zemel | A61B 18/1206 606/41 |
| 2017/0113035 | A1 | 4/2017 | Bonner et al. | |
| 2018/0000509 | A1 | 1/2018 | Fletcher et al. | |
| 2018/0056051 | A1 | 3/2018 | Kabra | |
| 2018/0177516 | A1 * | 6/2018 | Vardi | A61B 34/73 |
| 2019/0374254 | A1 * | 12/2019 | Arevalos | A61B 17/32002 |
| 2020/0315652 | A1 | 10/2020 | Vetter et al. | |
| 2021/0315629 | A1 | 10/2021 | Yang et al. | |
| 2021/0369321 | A1 | 12/2021 | Yang et al. | |

OTHER PUBLICATIONS

National Heart, Lung, and Blood Institute (NHLBI), "Basilica Procedure", Facebook, Jun. 17, 2019, 2 pp., https://fb.watch/fr4FRHXgVw/.

U.S. Appl. No. 63/254,247, filed Oct. 11, 2021, naming inventors Yang et al.

International Preliminary Report on Patentability from International Application No. PCT/US2022/030768 dated Dec. 7, 2023, 10 pp.

* cited by examiner

406

404

402

INTERATRIAL MULTI-CUSPID VALVULAR SHUNT

This application claims the benefit of U.S. Provisional Application Ser. No. 63/192,218, filed May 24, 2021, the entire content of which is incorporated herein by reference.

TECHNICAL FIELD

This disclosure generally relates to medical devices and, more particularly, to medical devices and associated techniques for forming shunts.

BACKGROUND

Pulmonary edema (or "oedema") is an excessive build-up of fluid in the lungs of a patient. Pulmonary edema may result from one or more conditions, including left atrial pressure elevation due to heart failure. A heart of a patient with heart failure may not efficiently pump blood, which may cause a pressure build-up in the left atrium and may cause fluid to be pushed into the lungs. Patients experiencing heart failure and pulmonary edema currently have limited treatment options.

Interatrial shunting is a technique to decompress the left or right atria in patients suffering from heart failure. During the procedure, a blood flow pathway is created between the right atrium and the left atrium such that blood flows between them. In a typical procedure, the septal wall separating the atria is cut with a puncturing device and a mechanical device such as a stent is left in place to prevent tissue overgrowth and to maintain the shunt.

SUMMARY

The present disclosure describes systems, devices, and techniques for creating a fluid pathway, or shunt, between the left atrium and right atrium of a heart of a patient. The shunt can be used to, for example, treat patients having heart failure and/or pulmonary edema. While typical shunting procedures may result in tissue overgrowth thus reducing the effectiveness of the shunt, in examples described herein, a medical system includes a cutting tool configured to puncture through a target treatment site and cut septal wall tissue to form a multi-cuspid valvular shunt in the septal wall, and an ablation device configured to ablate septal wall tissue of at least a portion of the multi-cuspid valvular shunt to make the multi-cuspid valvular shunt biostable, e.g., to inhibit overgrowth, scarring, and/or attachment of the cut portions of the septal wall tissue to reduce and/or prevent the multi-cuspid valvular shunt from closing.

In some examples, the cutting tool includes a plurality of expandable members positioned circumferentially about an elongated support member. Each of the expandable members includes a cutting member, and at least a portion of each of the expandable members is configured to radially extend from the elongated support member and to form the multi-cuspid valvular shunt, e.g., via cutting septal wall tissue with the cutting members. In some examples, the cutting members include an ablation electrode configured to cut septal wall tissue via a plasma cut and to ablate at least a portion of the cut septal wall tissue, e.g., along the cut edges, substantially concurrently with cutting the septal wall tissue. In other examples, the medical system includes an ablation device separate from the cutting tool, such as a radiofrequency, microwave, and/or pulsed field ablation device, a cryogenic ablation device, or the like. In some examples, the ablation device is configured to ablate a portion of, or all of, the septal wall tissue comprising the multi-cuspid valvular shunt, before or after the cutting tool cuts the septal wall tissue to form the multi-cuspid valvular shunt.

In some examples, the plurality of expandable members of the cutting tool are located at a distal portion of the elongated support member, and a distal end of each of the plurality of expandable members are attached to the elongated support member, e.g., at or near the distal end of the elongated support member. A proximal end of each of the plurality of expandable members is attached to a movable member that is configured to move axially towards and away from the distal end of the elongated support member to axially compress and extend each of the plurality of expandable members along the longitudinal axis. A portion of each of the plurality of expandable members is configured to radially extend away from the elongated support member upon being compressed in the axial direction to a deployed configuration by the movable member and to radially retract towards the elongated support member upon being extended in the axial direction to a delivery configuration via the movable member. In some examples, the elongated support member and movable member are configured to move axially relative to each other via rotation of a threaded shaft, one or more pull wires, or the like.

In one example, this disclosure describes a method including: cutting a septal wall between a right atrium and left atrium of a heart of a patient, wherein cutting the septal wall forms a multi-cuspid valvular shunt; and ablating septal wall tissue of at least a portion of the multi-cuspid valvular shunt, wherein the ablated tissue causes the at least a portion of the multi-cuspid valvular shunt to be biostable.

In another example, this disclosure describes a medical system including: a catheter defining a lumen; a first inner member configured to be received in the catheter lumen and extend distally outward from a distal opening of the catheter, wherein the inner member comprises: an elongated support member configured to move axially within the catheter lumen, the elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a cutting member configured to cut a septal wall tissue; and a second inner member configured to be received in the catheter lumen and extend distally outward from a distal opening of the catheter, wherein the first inner member is configured to form a multi-cuspid valvular shunt in the septal wall tissue, wherein the second inner member is configured to ablate at least a portion of the multi-cuspid valvular shunt such that the multi-cuspid valvular shunt is biostable.

In another example, this disclosure describes a medical device including: an elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a plasma cutting element configured to cut a septal wall tissue via plasma cutting to form a multi-cuspid valvular shunt in the septal wall tissue, wherein the plasma cutting element is configured to ablate only a portion of the multi-cuspid valvular shunt along the cut edges of the septal wall tissue such that the multi-cuspid valvular shunt is biostable.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1A:
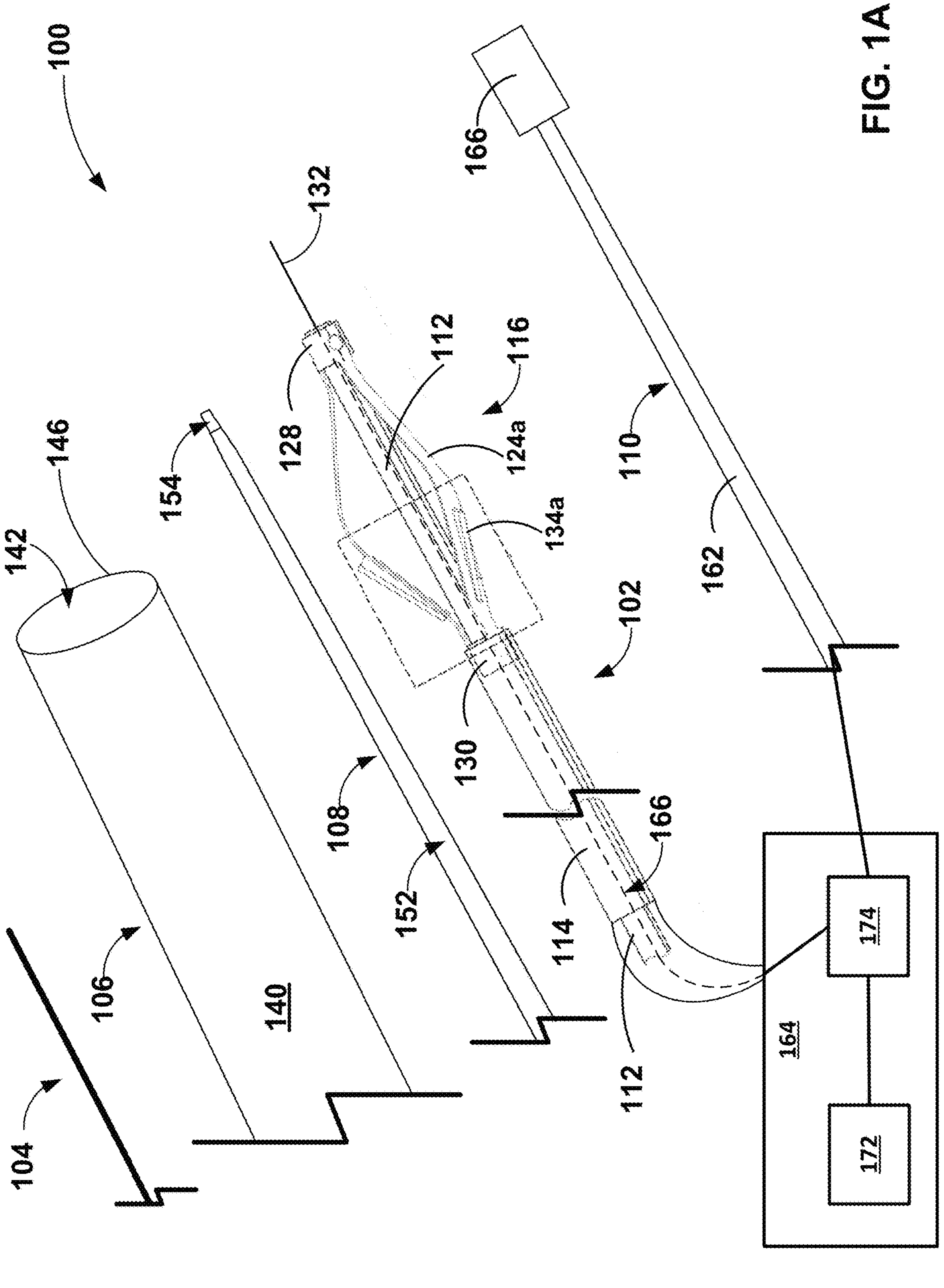
FIG. 1A is a perspective view depicting an example medical system configured to form a shunt at a target treatment site.

The disclosure describes examples of medical systems, devices, and techniques for creating a fluid pathway, or shunt, between the left atrium and right atrium of a heart of a patient without the use of an implant, e.g., such as a stent to maintain the shunt. The shunt may be formed as a valve, e.g., a multi-cuspid valve, in a septal wall between the left and right atrium, and at least a portion of the valve may be ablated. Example medical systems, devices, and techniques include ablating at least a portion of the valve to stabilize and/or make the valve biostable, e.g., to prevent tissue overgrowth of the septal wall in process of wound healing that leads to fusing together and closing of the valve. For example, medical systems, devices, and techniques include ablating to cause scarring, lesions, or the like, that prevent the tissue from fusing together and closing the valve. In some examples, medical systems, devices, and techniques include ablating at least a portion of the valve to stabilize and/or make the valve biostable for a period of time, e.g., after underlying causes of a pressure differential between left and right atria are removed and/or eliminated and a shunt is no longer needed. For example, after a period of time, the pressure differential between the left and right atria may reduce, and the biostabilized leaflets, tissue flats, and/or cuspids may be in contact for longer periods of time, which may promote fusing. In other examples, after the period of time and reduction of the pressure differential, surgical and/or pharmaceutical treatments may be used to further promote fusing.

In accordance with example medical systems, devices, and techniques described herein, septal wall tissue may be ablated via delivering energy (e.g., radiofrequency (RF) energy, plasma energy, or the like), or via cryoablation (e.g., via a cryogenic device such as a cryogenic balloon) to ablate a portion of the valve, e.g., septal wall tissue forming the valve. Due to the nature of the ablation, the tissue adjacent to the ablation will fibrose/endothelialize and define an opening (e.g., a shunt) which may be formed as a multi-cuspid valve between the left atrium and the right atrium, enabling pressure from the left atrium to decompress into the right atrium. This may help treat heart failure and/or pulmonary edema, such as by mitigating a mechanism of heart failure and/or pulmonary edema. In other examples, the systems, devices, and techniques described herein can be used to create a shunt between two other hollow anatomical structures of a patient and to treat other patient conditions. Thus, while a shunt between a left atrium of a heart of a patient and a right atrium of the patient is primarily referred to herein, the systems, devices, and techniques can be used to form shunts in other locations of the heart, other locations of the body of patients, or for other medical procedures in other examples.

In examples described herein, a medical system includes a puncture tool configured to create an initial puncture through a septal wall between the left atrium wall and a right atrium. The medical system also includes a cutting tool and an ablation device configured to form the shunt at the initial puncture site. For instance, the cutting tool may be configured to be extended through the initial puncture in a delivery configuration, then extended to a deployed configuration, and drawn back to cut septal wall tissue to form a multi-cuspid valvular shunt. In other examples, a separate ablation tool may be used to ablate at least a portion of the multi-cuspid valvular shunt, e.g., septal wall tissue at the edges of the cuts, septal wall tissue proximate the edges of the cuts, or the entire portion of septal wall tissue comprising the multi-cuspid valvular shunt. In some examples, the ablation tool may ablate septal wall tissue before the cutting tool cuts septal wall tissue. In other examples, the cutting tool cuts septal wall tissue before the ablation tool ablates septal wall tissue. In other examples, cutting and ablation of septal wall tissue may occur at least partially at the same time. For example, the cutting tool may also be configured to ablate (e.g., to be combination cutting/ablation tool) and may be used to ablate at least a portion of the multi-cuspid valvular shut, e.g., septal wall tissue at the edges of the cuts, while cutting septal wall tissue, or just before or after cutting septal wall tissue.

The techniques of this disclosure can be used to treat pulmonary edema. For instance, forming a shunt between the left atrium and the right atrium with the systems and devices described herein enable the relief of fluid build-up in the lungs of a patient without requiring the permanent implantation of a foreign object (e.g., a stent or the like), leading to better patient outcomes. In addition, the systems and devices described herein are highly user-friendly, e.g., do not require extensive training for the clinician.

Figure 1B:
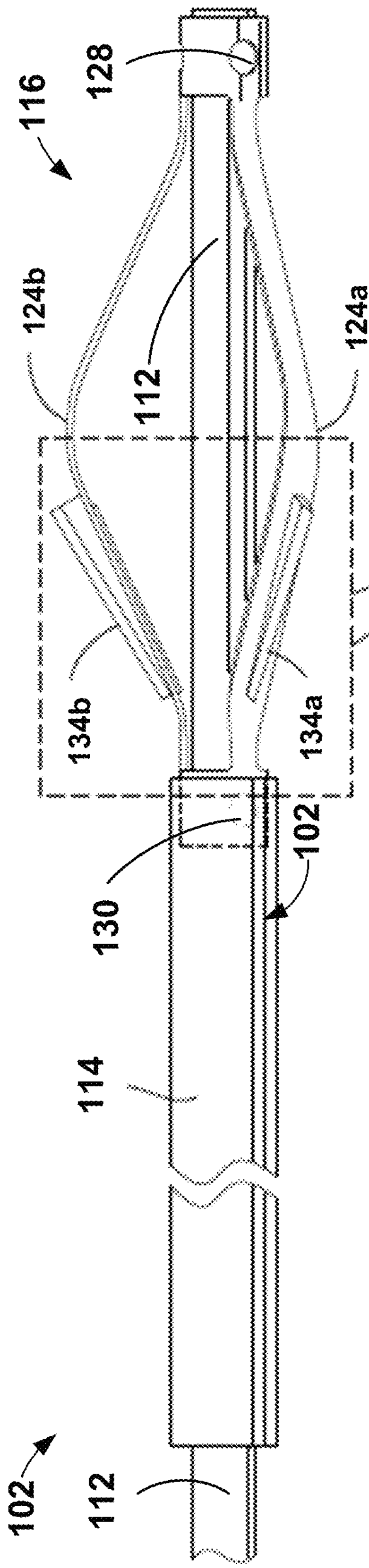
FIG. 1B is a perspective view depicting an example medical system, including a cutting tool.
Figure 1C:
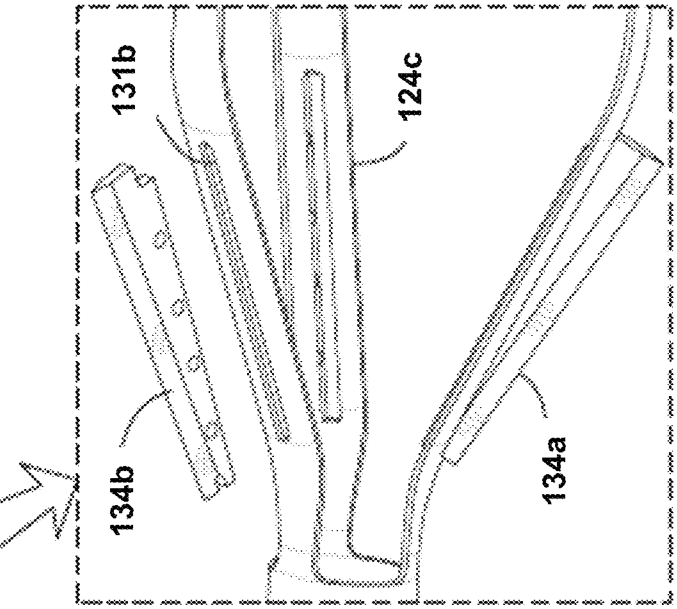
FIG. 1C is an enlarged perspective view depicting the cutting tool of FIG. 1A.

FIG. 1A is a perspective view depicting an example medical system 100 configured to form a shunt at a target treatment site between a left atrium and a right atrium of a heart of a patient. FIG. 1B is a perspective view depicting an example inner member 102 of medical system 100 of FIGS. 1A, and 1C is an enlarged perspective view depicting expandable members 124 and cutting members 134 of inner member 102 of FIG. 1A. In the examples shown in FIGS. 1A-1C, medical system 100 includes inner member 102, which may be an example of a cutting tool, and inner member 110, which may be an example of an ablation tool. In some examples, but not all examples, medical system 100 also includes a separate puncturing tool 108. In other examples, puncturing tool 108 may be part of inner member 102 or a different device, such as a separate ablation device. Medical system 100 is also shown in FIG. 1A as including a guidewire 104, a delivery sheath 106, and a power generator 164.

In the examples shown in FIGS. 1A-1C, inner member 102 includes an elongated support member 112, a movable member 114, and a distal portion 116. In some examples, elongated support member 112 defines a device inner lumen configured to receive, e.g., a guidewire 104 and/or puncturing tool 108. Guidewire 104 can, for example, be used to help navigate inner member 102 through vasculature of a patient to a target treatment site within the patient. Elongated member 112 is at least partially within a lumen of movable member 114, and inner member 102 is configured to be movable within a lumen 142 of catheter 140.

Distal portion 116 is coupled to elongated support member 112, e.g., at attachment portion 128 at a distal end of distal portion 116 and a distal end of elongated support member 112 as shown. Distal portion 116 is coupled to movable member 114, e.g., at attachment portion 130 at a proximal end of distal portion 116 and a distal end of movable member 114 as shown. In some examples, as detailed further below, one or both of movable member 114 and elongated support member 112 are configured to be longitudinally translatable along a longitudinal axis 166 defined by elongated support member 112 to change a configuration of distal portion 116, e.g., between a delivery configuration and a deployed configuration. For example, distal portion 116 includes a plurality of expandable members 124 positioned circumferentially about elongated support member 112. At least a portion of each of the plurality of expandable member 124 is configured to radially extend and/or move in the radial direction to and from elongated support member 112, e.g., upon compression and/or tension of the plurality of expandable members due to longitudinal translation of movable member 114 relative to elongated support member 112.

In the example shown, expandable members 124 are in a deployed configuration in which a portion (e.g., the non-attached portions) of each of expandable members 124 extend radially away from elongated support member 112, e.g., expandable members 124 are "expanded" radially. In the deployed configuration, elongated support member 112 and movable member 114 are longitudinally translated relative to each other such that attachment portions 128 and 130 are moved nearer to each other compressing expandable members 124 and causing the expandable members to move radially away from elongated support member 112. To change distal portion 116 to a delivery configuration, a user may translate elongated support member 112 and movable member 114 relative to each other such that attachment portions 128 and 130 are moved farther from each other and exerting tension on expandable members 124 and causing the expandable members to move radially towards elongated support member 112. In the delivery configuration, expandable members 124 may be substantially adjacent to and substantially straight along an outer surface of elongated support member 112. In other words, in the delivery configuration the expandable members 124 may be configured to be retracted so as to fit and be movable within lumen 142 of catheter 106. Each of expandable members 124 may be coupled and/or attached to movable member 114 and elongated support member 112 as described above relative to distal portion 116.

In some examples, elongated support member 112 includes an atraumatic distal tip or distal portion, e.g., formed from a relatively soft polymer material (not shown). In some examples, a distal guidewire 132, such as a Nitinol wire or another elongated guide member, extends distally outward from a distal-most end of elongated support member 112. Guidewire 132 can be, for example, embedded in elongated support member 112 or extend through a lumen defined by elongated support member 112 and extend distally outward from a distal mouth or opening of elongated support member 112. In some examples, guidewire 132, in addition to, or instead of, puncturing tool 108, is configured to function as a puncturing element configured to puncture through tissue, e.g., septal wall tissue, of a patient to enable advancement of at least distal portion 116 and elongated support member 112 through the tissue. In some examples, guidewire 132 may be a conductor and may be configured to be electrified and/or heated.

Expandable members 124 may be made of a metal, a plastic, or any suitable material with sufficient stiffness to support cutting members 134 to cut tissue of a patient and sufficient flexibility and/or elasticity to expand and contract radially in response to longitudinal compression and tension, as described herein. In some examples, expandable members 124 may be made of Nitinol. Although illustrated and described as having three expandable members 124*a*, 124*b*, and 124*c* (collectively "expandable members 124"), distal portion 116 may include fewer or more expandable members 124, e.g., one expandable member 124, two expandable members 124, or four or more expandable members 124.

In the examples shown, expandable members 124 each include cutting members 134 configured to cut tissue of the patient, e.g., septal wall tissue. For example, expandable member 124*a* includes cutting member 134*a*, expandable member 124*b* includes cutting member 134*b*, and expandable member 124*c* includes cutting member 134*c*. Cutting members 134*a*, 134*b*, and 134*c* (collectively "cutting members 134") may be made of a metal, a plastic, or any suitable material for cutting tissue of the patient. In some examples, cutting members 134 may be blades, e.g., formed as razor blades having a razer and/or very thin and relatively hard cutting edge. In the examples shown, cutting members 134 are attached to expandable members 124, e.g., via mounting slots 131 illustrated in FIG. 1C. In the example shown, cutting members 134 are positioned on a proximal portion of expandable members 124 such that in the deployed configuration (as shown), the cutting edges of cutting members 134 are angled towards the proximal direction, e.g., inner member 102 is configured to cut septal wall tissue when moved proximally, or "drawn back," with expandable members 124 in the deployed configuration. In other examples, cutting members 134 may be positioned on a distal portion of expandable members 124 such that in the deployed configuration, the cutting edges of cutting members 134 are angled towards the distal direction, e.g., inner member 102 is configured to cut septal wall tissue when moved distally, or "pushed forward," with expandable members 124 in the deployed configuration. In some examples, cutting members 134 may be plasma cutting elements rather than mechanical cutting elements such as blades. For examples, cutting members 134 may include a plasma electrode, a channel configured to guide a stream of pressurized gas (such as argon), one or more nozzles for injecting/receive gas to and/or from the channel, and/or any other means for creating an electrical channel of heater or superheated, electrically ionized gas, e.g., a plasma, or plasma "blade" comprising a plasma localized to a plasma electrode and/or channel. In other examples, cutting members 134 may be integral with expandable members 124, e.g., a portion of the length of expandable members 124 may be configured to cut septal wall tissue and may not include separate cutting members such as blades.

Figure 4C:
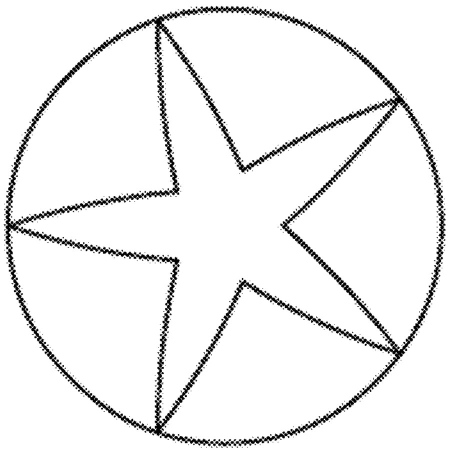
FIG. 4C is a cross-sectional schematic view depicting another example interatrial multi-cuspid valvular shunt.
Figure 4B:
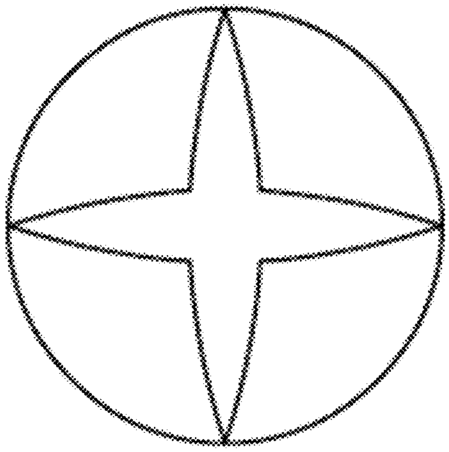
FIG. 4B is a cross-sectional schematic view depicting another example interatrial multi-cuspid valvular shunt.
Figure 4A:
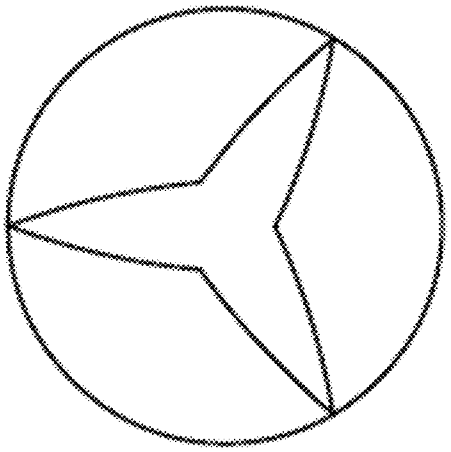
FIG. 4A is a cross-sectional schematic view depicting an example interatrial multi-cuspid valvular shunt.

Referring now to FIGS. 4A-4C, FIG. 4A is a cross-sectional schematic view depicting an example interatrial tri-cuspid valvular shunt 402, FIG. 4B is a cross-sectional schematic view depicting an example interatrial quadri-cuspid valvular shunt 404, and FIG. 4C is a cross-sectional schematic view depicting an example interatrial penta-cuspid valvular shunt 406. In some examples, inner member 102 is configured to form a multi-cuspid valvular shunt in septal wall tissue. For example, inner member 102 including three expandable members 124 as illustrated in FIGS. 1A-1C is configured to cut tri-cuspid valvular shunt 402. In other examples, inner member 102 may include four expandable members 124 and may be configured to cut quadri-cuspid valvular shunt 404. In still other examples, inner member 102 may include five expandable members 124 and may be configured to cut penta-cuspid valvular shunt 406.

Referring back to FIGS. 1A-1C, catheter 106 is configured to facilitate delivery of inner member 102, e.g., distal portion 116, to a target treatment site in a patient. Catheter 106 includes an elongated tubular body 140 defining a catheter inner lumen 142 and opening 146 to inner lumen 142.

In the examples shown in FIGS. 1A-1C, inner member 110 includes an elongated support member 162, and an ablation member 166. In some examples, elongated support member 162 defines a device inner lumen configured to receive, e.g., a guidewire 104 and/or puncturing tool 108. Guidewire 104 can, for example, be used to help navigate inner member 110 through vasculature of a patient to a target treatment site within the patient. Inner member 110 is configured to be movable within a lumen 142 of catheter 140.

Ablation element 166 is coupled to elongated support member 162, e.g., at a distal end of elongated support member 162 as shown. Ablation element 166 is configured to ablate tissue of the patient, e.g., septal wall tissue. In some examples, ablation element 166 is configured to deliver radiofrequency energy, microwave energy, pulsed electric field energy, e.g., for pulsed field ablation (PFA), or the like, to septal tissue to ablate septal tissue. In other examples, ablation element 166 is configured to cryoablate septal wall tissue, e.g., ablation element 166 may be a cryogenic element such as a cryogenic balloon.

Medical system 100 includes a puncturing element configured to form an initial puncture through septal wall tissue. For example, the puncturing element can have an incisive tip configured to cut a pathway through tissue of a patient and/or another type of tip configured to define the pathway through tissue. In some examples, but not all examples, the puncturing element includes a distinct puncturing tool 108, which is physically separate from inner member 102. In other examples, the puncturing element may be part of inner member 102, such as the distal guidewire 132 (e.g., a Nitinol flat wire) extending from an atraumatic distal tip of elongated support member 112 of inner member 102.

As shown in FIG. 1, puncturing tool 108 includes an elongated structure 152, such as a guidewire, a hypotube, a catheter body, or the like, and an electrifiable distal tip 154, which is configured to electrically heat to facilitate the forming of a puncture through septal wall tissue. For instance, the electrifiable distal tip 154 may include a plasma electrode. In other examples, distal tip 154 is a relatively sharp incisive tip facilitating puncture through purely mechanical means.

In some examples, puncturing tool 108 further includes a dilation element (not shown), which is configured to expand radially outward to expand a puncture formed by puncturing tool 108. In some examples, the diameter of puncturing tool 108 may increase in a proximal direction from the distal end of puncturing tool 108 to dilate an initial puncture, e.g., puncturing tool 108 may have a tapered tip configured to dilate the initial puncture such as when puncturing tool is distally advanced through the puncture. In other examples, after distal tip 154 forms an initial puncture through septal wall tissue and the dilation element may be at least partially advanced through the puncture and expanded radially outward to dilate the puncture (forming a dilated puncture). The dilated puncture facilitates subsequent advancement of distal portion 116 of inner member 102 through the septal wall of the patient's heart. For example, the initial puncture formed by distal tip 154 may not be large enough to enable distal portion 116 to extend through the puncture.

Generator 164 includes control circuitry 172 and generation circuitry 174. In general, control circuitry 172 is configured to cause generation circuitry 174 to generate energy, e.g., monopolar and/or bipolar RF energy, electrical energy useable with the plasma element to create a plasma (e.g., an electrical channel of superheated, electrically ionized gas), or the like, and deliver the generated energy to distal portion 116 and/or ablation element 166. As described throughout this disclosure, control circuitry 172 may be configured to control, monitor, supply, and/or otherwise support operations of inner member 102, inner member 110, and generator 164, e.g., by determining and implementing parameters (e.g., magnitude, frequency, etc.) of energy for delivery to tissue at the target treatment site via system 100. For example, expandable members 124 may include a RF energy directing element, a pulsed-field ablation (PFA) element, a plasma element, or the like.

Control circuitry 172 can have any suitable configuration. In some examples, control circuitry 172 includes any of a microprocessor, integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 172 may include multiple components, such as any combination of one or more microprocessors, one or more DSPs, one or more ASICs, or one or more FPGAs, as well as other discrete or integrated logic circuitry, and/or analog circuitry.

Although not shown in FIG. 1, generator 164 can also include memory that stores instructions that are executable by control circuitry 172. When executed by control circuitry 172, such instructions may cause control circuitry 172 to provide the functionality ascribed to control circuitry 172 herein. The instructions may be embodied in software and/or firmware. The memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Figure 2:
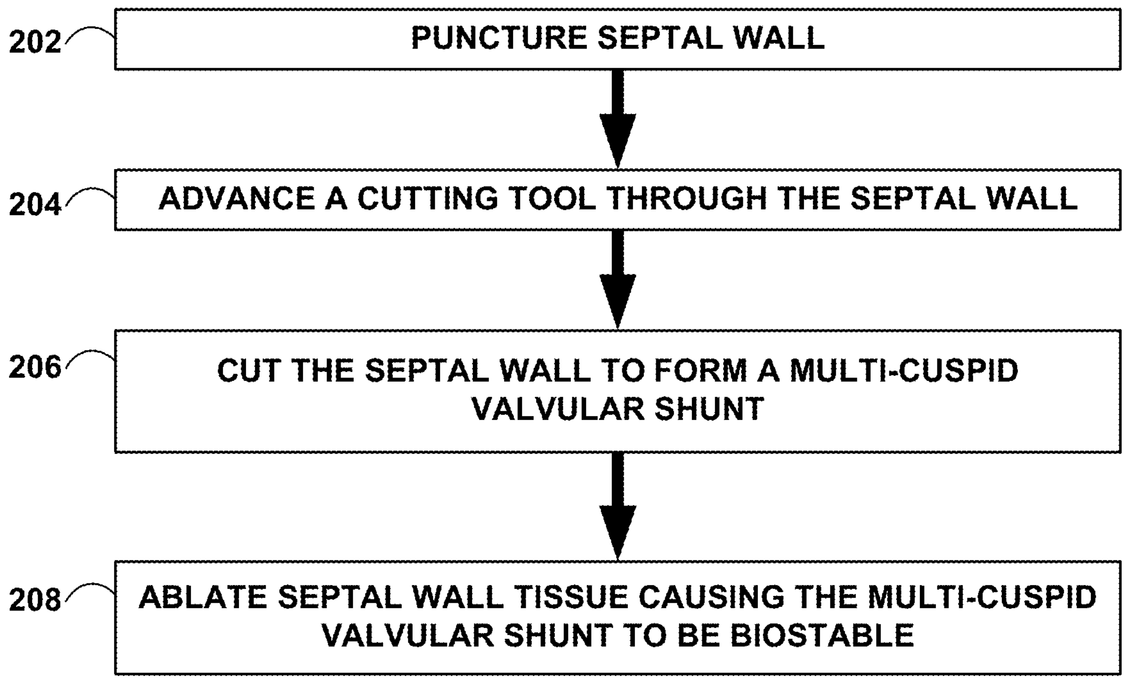
FIG. 2 is a flow diagram illustrating an example technique for forming a biostable, multi-cuspid valvular shunt between the left and right atria of a heart of a patient.
Figures 3A, 3B, 3C, 3D:
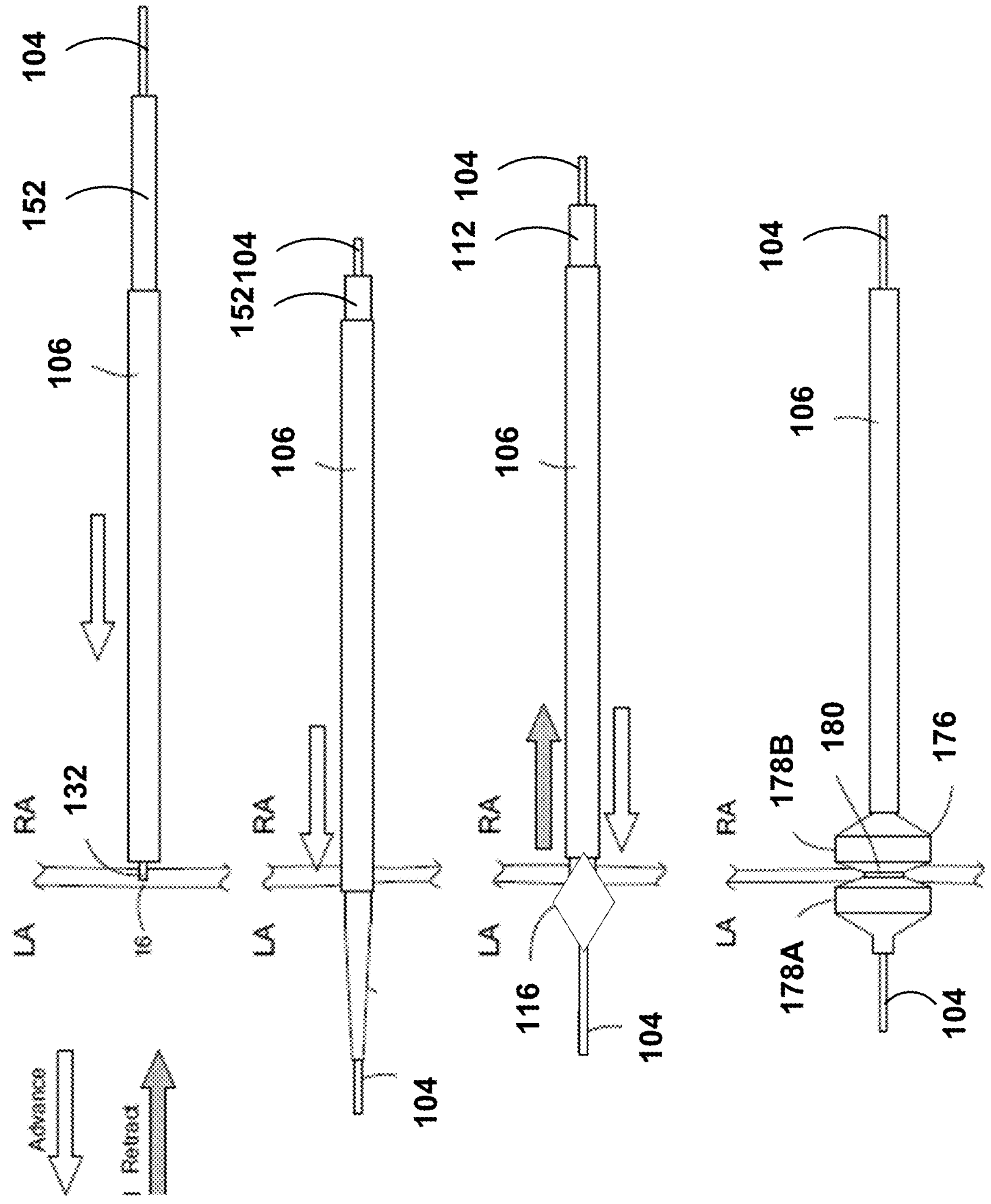
FIG. 3A is a schematic diagram illustrating penetrating a septal wall with an example medical system.
FIG. 3B is a schematic diagram illustrating extending a cutting tool of an example medical system in preparation for cutting a septal wall.
FIG. 3C is a schematic diagram illustrating cutting a septal wall with a cutting tool of an example medical system.
FIG. 3D is a schematic diagram illustrating an ablation tool of an example medical system ablating septal wall tissue after cutting the septal wall.

FIG. 2 is a flow diagram illustrating an example technique for forming a biostable, multi-cuspid valvular shunt between the left and right atria of a heart of a patient. FIGS. 3A-3D are schematic diagrams illustrating steps of the method of FIG. 2 using medical system 100 described above. The example technique of FIGS. 2-3D is described with reference to medical system 100, however, the example technique may be performed using any system including a device and/or tool including the functionality of inner member 102 described herein. The technique of FIGS. 2-3D may be performed by any suitable user, such as a cardiologist or other clinician.

A clinician may puncture a septal wall of a patient (202). For example, the clinician may advance catheter 106 to a septal wall between left and right atria of a patient's heart, e.g., through the femoral vein of the patient to access the right atrium. In some examples, the clinician may advance catheter 106 together with guidewire 104 to the septal wall between left and right atria. The clinician may advance puncture tool 108 with guidewire 104 and/or inner member 102 with guidewire 132 through lumen 142 of catheter 106 to the septal wall. The clinician may then advance puncture tool 108 and/or inner member 102 into the septal wall, and optionally electrify distal tip 154 or guidewire 132, to puncture the septal wall and form an opening in the septal wall. In other examples, the clinician may advance guidewire 104 into the septal wall, optionally electrify at least a distal portion of guidewire 104, to puncture the septal wall and form the opening, e.g., before or after insertion of and advancing inner member 102 to the septal wall through lumen 142. In some examples, the clinician may electrify distal tip 154, guidewire 132, or guidewire 104 via generator 164, or via any other source of electrical and/or radiofrequency energy. For example, the clinician may puncture the septal wall via RF ablation. In some examples, the clinician may use distal tip 154, guidewire 104, or guidewire 132 to pace the right atrium to locate the Fossa Ovalis for a target area to create an opening 16 in the septal wall. For example, distal tip 154, guidewire 104, or guidewire 132 may use unipolar pacing RF energy to acquire electrogram signals to locate the Fossa Ovalis. When the Fossa Ovalis (or other target area) is located, the clinician may use the same distal tip 154, guidewire 104, or guidewire 132 to use ablative RF energy to puncture the septal wall to create opening 16, as shown in FIG. 3A. In some examples, the clinician may dilate opening 16, e.g., via a separate dilator tool, using puncture tool 108, or using inner member 102.

The clinician may advance inner member 102 through the septal wall (204). For example, the clinician may retract and/or remove puncture tool 108 from catheter 106, if used at 202, and advance inner member 102 through lumen 142 of catheter 106 with distal portion 116 and expandable members 124 in a delivery configuration, e.g., unexpanded. The clinician may advance distal portion 116 through the puncture/opening in the septal wall, e.g., from the right atrium to the left atrium, as shown in FIG. 3B.

The clinician may cut the septal wall between a right atrium and left atrium of the heart of a patient and form a multi-cuspid valvular shunt (206). For example, the clinician may cause expandable members 124 to expand radially away from elongated support member 112, and retract inner member 102 back through the septal wall to cut the septal wall with cutting members 134. The expandable members 124 may be circumferentially positioned about elongated support member 112 every 120 degrees, e.g., three expandable members 124 may be evenly spaced about elongated member 112 such that multi-cuspid valvular shunt 402 is formed. In other examples, inner member 102 may include four or five expandable members such that the clinician may form multi-cuspid valvular shunt 404 or 406, respectively, after cutting the septal tissue.

Figure 5A:
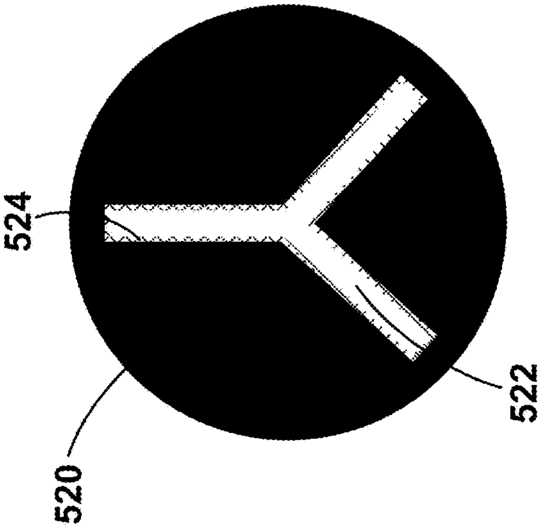
FIG. 5A is a cross-sectional schematic view depicting an example biostable interatrial multi-cuspid valvular shunt.

In some examples, cutting members 134 may be plasma elements, and control circuitry 172 may cause the plasma elements to both cut the septal tissue and ablate the septal tissue, e.g., along the edges of the cuts in the septal tissue, with a plasma and/or plasma energy. For example, the clinician may cut the septal wall and ablate septal wall tissue concurrently, e.g., method steps (206) and (208) (further described below) may occur at least partially at the same time. FIGS. 5A-5E are cross-sectional schematic views depicting ablation of different portions of a septal wall prior to, during, or after cutting the septal wall to form a biostable interatrial multi-cuspid valvular shunt. Referring to FIG. 5A, at (206), the clinician may cut the septal wall tissue 520 with cutting members 134 as plasma elements, e.g., plasma cutting and ablating septal tissue 520, and ablate only septal wall tissue along the edges, e.g., illustrated as ablated tissue 524 in FIG. 5A, of the cut septal wall tissue 522 to form biostable interatrial multi-cuspid valvular shunt 502.

Referring back to FIG. 2, the clinician may ablate septal wall tissue of at least a portion of the multi-cuspid valvular shunt, wherein the ablated tissue causes the at least a portion of the multi-cuspid valvular shunt to be biostable. For example, the clinician may cut septal wall tissue to form multi-cuspid valvular shunt 508 illustrated in FIG. 5D, and subsequently ablate substantially all of the septal wall tissue comprising multi-cuspid valvular shunt 508 to biostabilize the shunt and form biostable multi-cuspid valvular shunt 510 illustrated in FIG. 5E. For example, the clinician may retract expandable members 124 to be in the delivery configuration, and remove inner member 102, e.g., via catheter 106. The clinician may then advance inner member 110 through lumen 142 of catheter 106 to the cut septal wall tissue. The clinician may then use ablation member 166 to ablate septal wall tissue to biostabilize the shunt. In some examples, ablation member 166 may be a cryogenic balloon 176 (e.g., as illustrated in FIG. 3D). Cryogenic balloon 176 may include a pair of longitudinally spaced lobes 178A and 178B with a middle portion 180 disposed therebetween, each of the pair of lobes 178A and 178B defining a first diameter and the middle portion 180 defining a second diameter less than the first diameter. The clinician may advance the balloon at least partially through opening 16 and inflate balloon 176 such that the first and second lobes 178A and 178B abut each other on opposite sides of the septal wall. Further details about the balloon 176 may be found in U.S. patent application Ser. No. 17/182,594, the entirety of which is expressly incorporated by reference herein. The clinician may then introduce a cooling agent, such as a refrigerant, into lobes 178A and 178B to ablate both sides of the septal wall to biostabilize the multi-cuspid interatrial shunt. In other examples, the clinician may perform method steps (206) and (208) in reverse order, e.g., ablating septal wall tissue 520 to form ablated septal wall tissue 524 using inner member 110 prior to cutting septal wall tissue 522 using inner member 102, and in some examples prior to puncturing the septal wall, as described above to form biostable interatrial multi-cuspid valvular shunt 510.

Figure 5B:
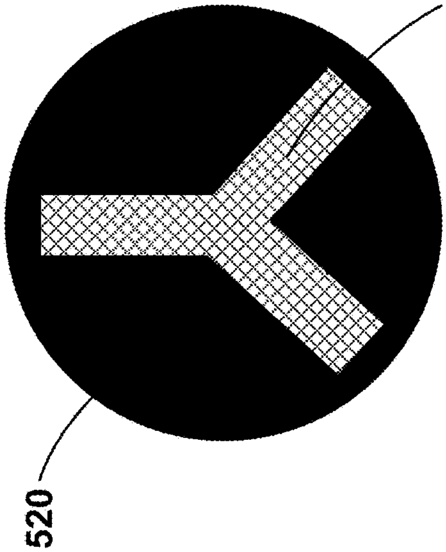
FIG. 5B is a cross-sectional schematic view depicting ablation of a portion of a septal wall prior to cutting the septal wall to form a biostable interatrial multi-cuspid valvular shunt.
Figure 5C:
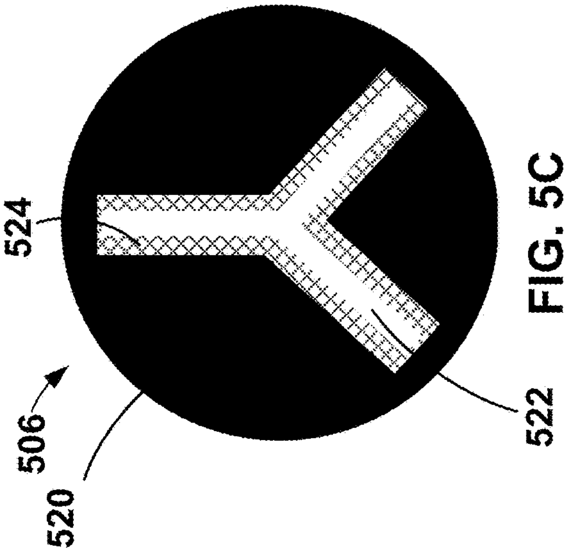
FIG. 5C is a cross-sectional schematic view depicting an example biostable interatrial multi-cuspid valvular shunt after cutting the septal wall of FIG. 5B.
Figure 5D:
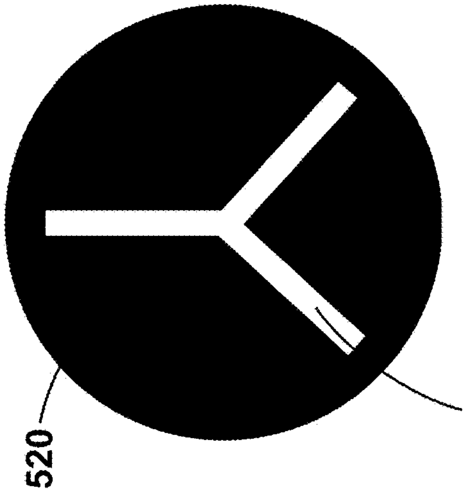
FIG. 5D is a cross-sectional schematic view depicting an example interatrial multi-cuspid valvular shunt after cutting and before ablation of a portion of septal wall tissue including the interatrial multi-cuspid valvular shunt.
Figure 5E:
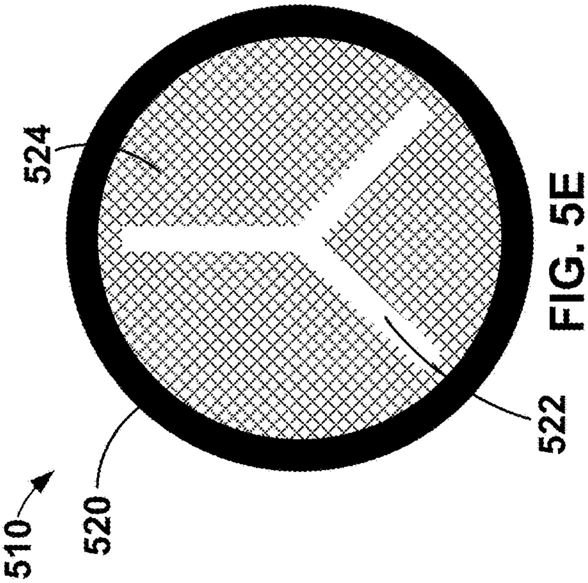
FIG. 5E is a cross-sectional schematic view depicting an example biostable interatrial multi-cuspid valvular shunt after ablation of the interatrial multi-cuspid valvular shunt of FIG. 5D.

In some examples, ablation element 166 comprises a RF ablation element, a microwave ablation element, or a PFA element. For example, the clinician may ablate septal wall tissue corresponding to portions of septal tissue 520 to be cut, e.g., ablated septal tissue 524 illustrated in FIG. 5B, and subsequently cut the septal wall tissue at ablated septal tissue 524 to form multi-cuspid valvular shunt 506. In some examples, the clinician may use ablation member 166 to ablate septal wall tissue using a RF ablation element, a microwave ablation element, or a PFA element to biostabilize the shunt before or after cutting the septal wall tissue using inner member 102. In some examples, the clinician may ablate only an area of septal wall tissue corresponding to the circumferential positions of the plurality of cutting members and a radial extent of the plurality of cutting members, e.g., ablated septal wall tissue 524 as illustrated in FIG. 5B.

Figure 6:
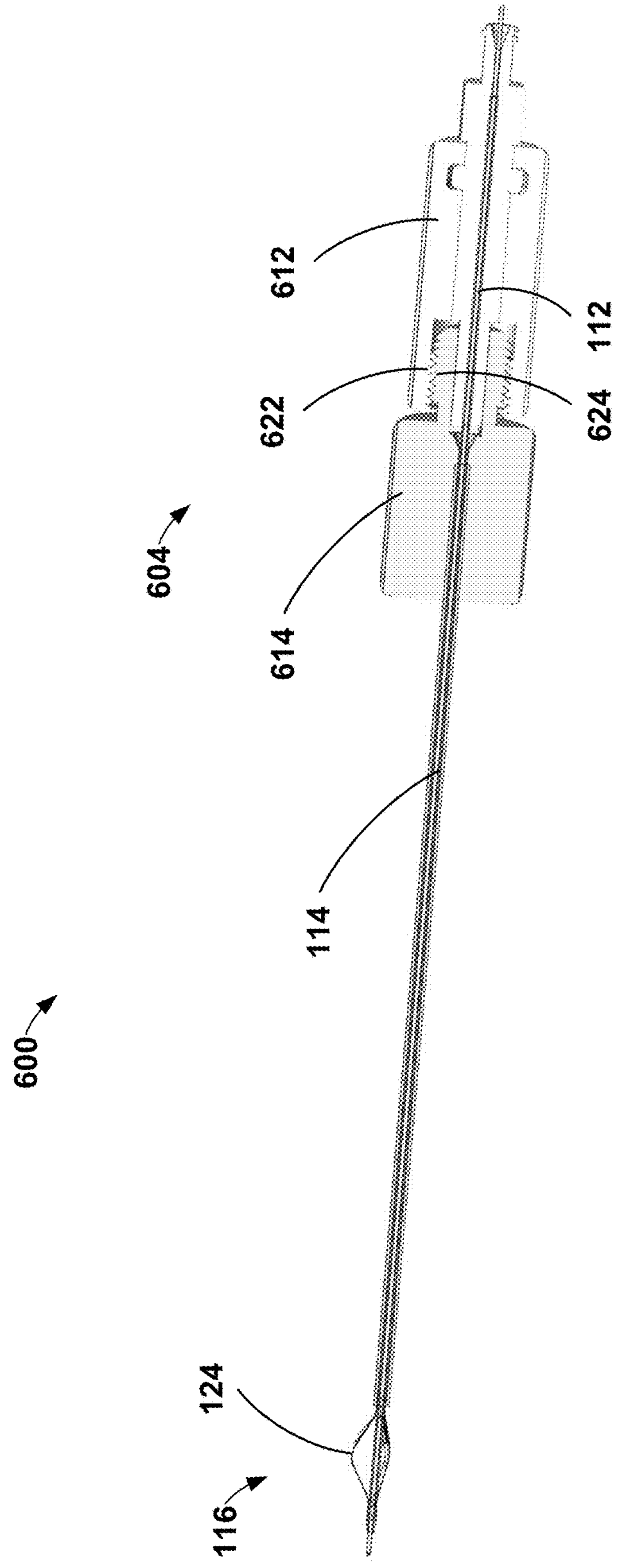
FIG. 6 is a schematic perspective view depicting an example medical system including an example deployment mechanism.

FIG. 6 is a schematic cross-sectional view depicting an example medical system 600 including an example deployment mechanism 604. Medical system 600 may be substantially similar to medical system 100 of FIGS. 1A-1C and including deployment mechanism 604. In the example shown, deployment mechanism 604 includes a first portion 612 that may be integral with and/or attached to elongated support member 112. Deployment mechanism 604 includes a second portion 614 that may be integral with and/or attached to movable member 114. Second portion 614 comprises a movable shaft including threads 624, and first portion 612 comprises a movable shaft including threads 622. Upon rotation of first portion 612 in a first direction relative to second portion 614, first portion 612 and elongated support member 112 are configured to move in an axial direction, e.g., along the longitudinal length of movable member 114 and elongated support member 112, in a distal direction relative to movable member 114, thereby causing expandable members 124 to retract to the delivery configuration. Upon rotation of first portion 612 in a second direction opposite the first direction relative to second portion 614, first portion 612 and elongated support member 112 are configured to move in an axial direction, e.g., along the longitudinal length of movable member 114 and elongated support member 112, in a proximal direction relative to movable member 114, thereby causing expandable members 124 to expand to the deployed configuration, as shown in FIG. 6. In other examples, (not shown), medical system 100 and/or 600 may include at least one wire attached to elongated support member 112 and configured to proximally move elongated support member 112 relative to movable member 114 to cause expandable members 124 to expand to the deployed configuration. The at least one wire may be configured to release the elongated support member 112 to distally move relative to the movable member 114, e.g., via elasticity of expandable members 124, to cause expandable members 124 to retract to the delivery configuration.

Figure 7:
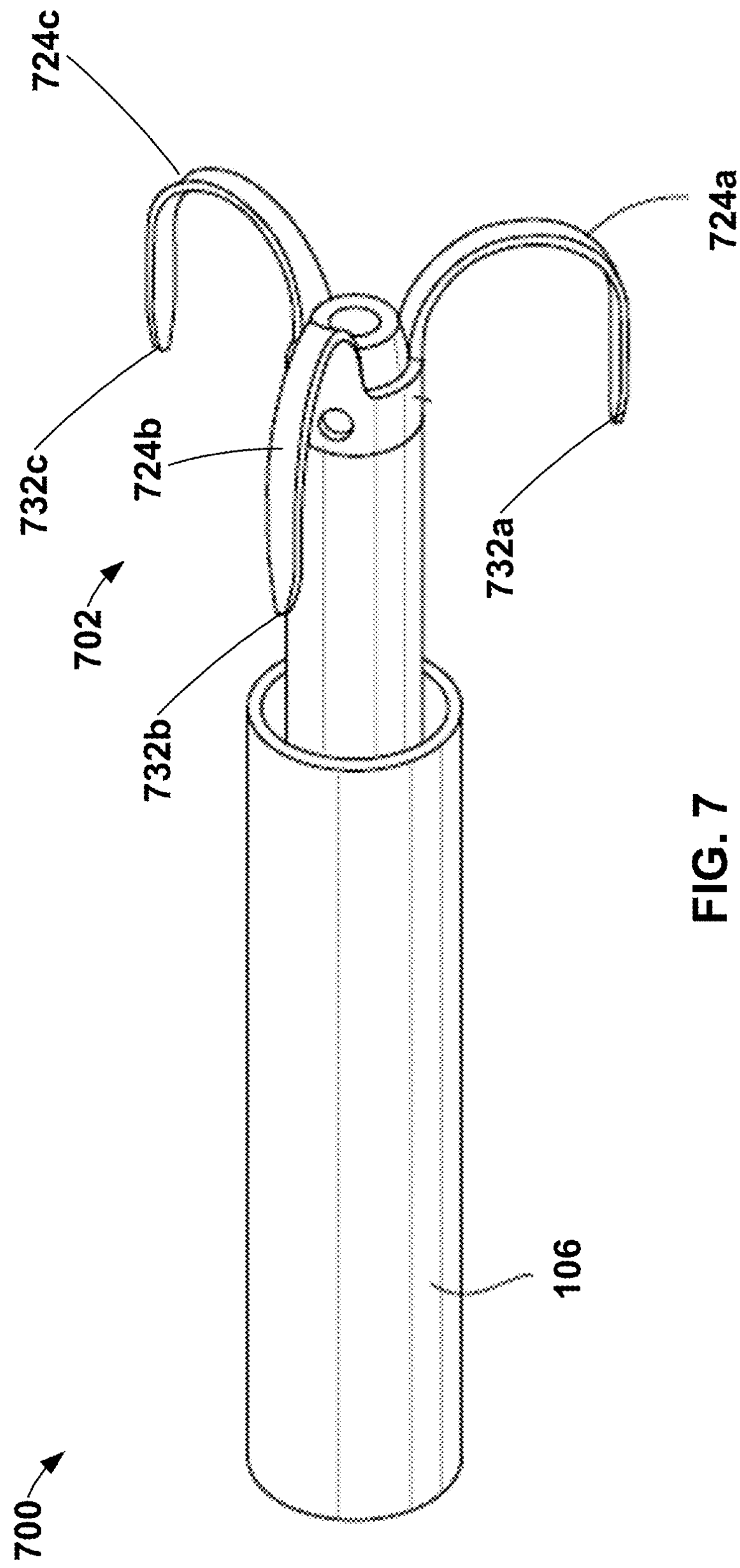
FIG. 7 is a perspective view depicting another example medical system, including a cutting tool.

FIG. 7 is a perspective view depicting another example medical system 700, including a cutting tool 702. Medical system 700 may be substantially similar to medical system 100 described above except with expandable members 724 being curved tines in a deployed configuration. The expandable members 724 may be flexible and take the shape illustrated in FIG. 7 upon being advanced out of lumen 142 of catheter 106, and to straighten, e.g., to a delivery configuration, upon being retracted into lumen 142, e.g., after cutting septal tissue as described above with reference to expandable members 124. For example, tips 732*a*, 732*b*, and 732*c*, collectively "tips 732," may be sharp and/or configured to cut tissue, such as septal wall tissue. In some examples, expandable members 724 may be in the delivery configuration and within lumen 142 of catheter 106. Catheter 106, including cutting tool 702 and expandable members 724 within lumen 142 in the delivery configuration may be delivered from the right atrium through the septum into the left atrium, e.g., after the septum has been punctured. Expandable members 724 may then be pushed out of lumen 142 of catheter 106 and may expand to the deployed configuration, e.g., the shape illustrated in FIG. 7. Medical system 700 may then be retracted back towards the right atrium, and tips 732 may penetrate the septum. As the medical system 700 and expandable members 724 are retracted, the hook shapes may pull through the septum causing a cut or tear from the points of the tip punctures to the center, e.g., the punctured hole.

Figure 8A:
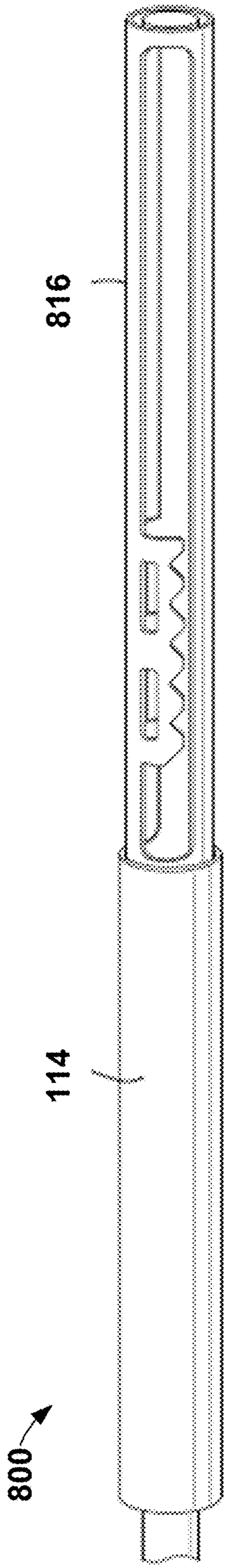
FIG. 8A is a perspective view depicting another example medical system in a delivery configuration, including a cutting tool.
Figure 8B:
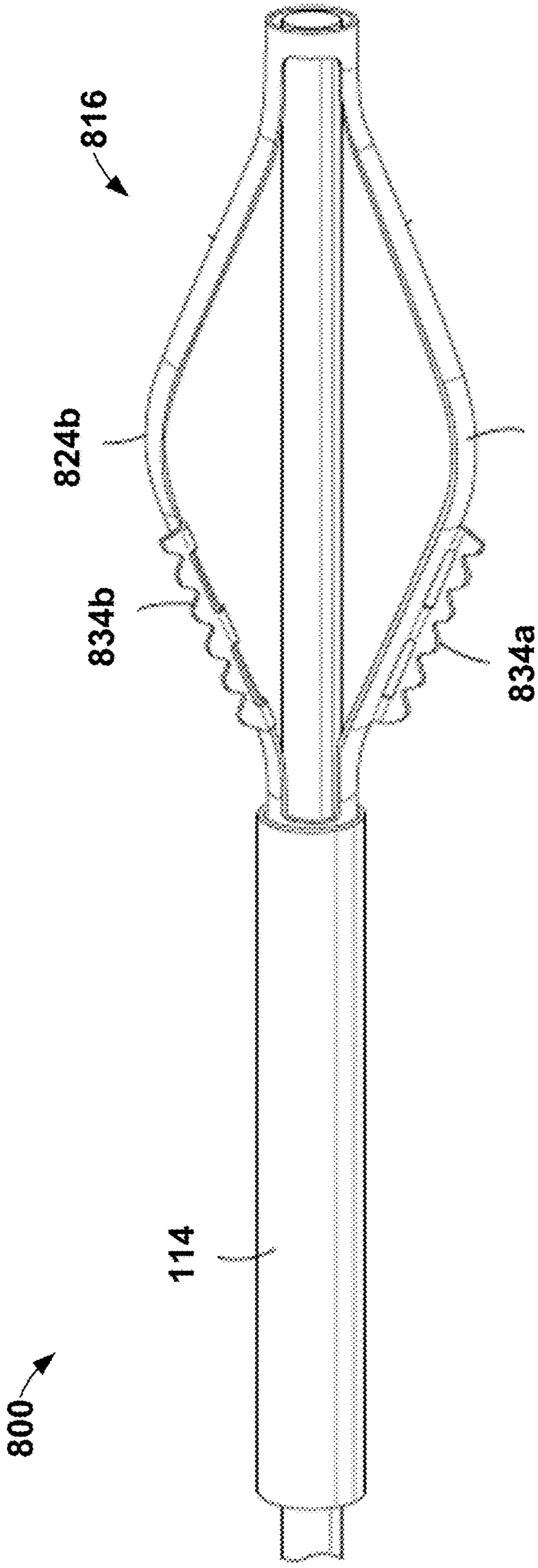
FIG. 8B is a perspective view depicting the example medical system of FIG. 8A in a deployed configuration, including a cutting tool.

FIG. 8A is a perspective view depicting another example medical system 800 in a delivery configuration, including a cutting tool 816, and FIG. 8B is a perspective view depicting the example medical system 800 of FIG. 8A in a deployed configuration, including the cutting tool 816. Medical system 800 may be substantially similar to medical system 100 described above except with cutting members 834 being serrated blades.

Figure 9:
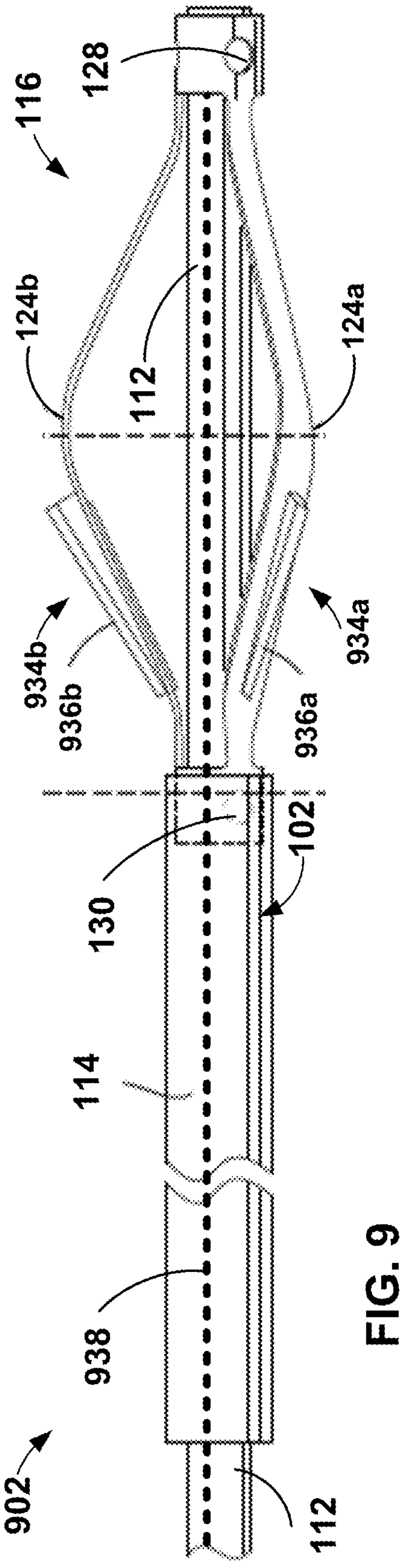
FIG. 9 is a perspective view depicting another example inner member.

FIG. 9 is a perspective view depicting another example inner member 902. Inner member 902 may be substantially similar to inner member 102 described above, except that inner member 902 includes cutting member 934*a*, cutting member 934*b*, and cutting member 934*c* (not visible in the example shown), collectively "cutting members 934," and energy source 938.

In the example shown, cutting members 934 are energized cutting elements configured to cut tissue of the patient, e.g., septal wall tissue. Energized cutting members 934 may be connected to energy source 938, e.g., an electrical conductor, which may be connected to generation circuitry 174 and configured to delivery electrical energy to cutting members 934. In the example shown, all conductive and/or metal components of distal portion 116 are coated with, and/or encapsulated within, a dielectric material, e.g., a polymer, polytetrafluoroethylene (PTFE), parylene, or the like, e.g., elongated support member 112, attachment portion 128, expandable members 124, and all portions of cutting members 934 except for surfaces 936*a*, 936*b*, and 936*c* (not visible in FIG. 9), collectively "surfaces 936." In some examples, surfaces 936 may comprise plasma cutting elements, e.g., a channel configured to guide a stream of a gas and at least one electrode configured to ionize the gas, and associated components for directing the gas (e.g., argon) through the channel, e.g., tubing, nozzles, and the like. In other examples, surfaces 136 may be heated via radiofrequency (RF) heating by a RF electrode, and/or surfaces 936 may comprise an edge portion of an RF electrode. In other examples, cutting members 934 may comprise electrical discharge machining (EDM) wires coated with a dielectric material except for surfaces 936. In some examples, electrically conductors comprising surfaces 936, electrodes configured to RF heat surfaces 936, and/or electrodes configured to generate a plasma comprising surfaces 936 are connected to energy source 938 and are configured to receive electrical energy via energy source 938.

In some examples, cutting members 934 are configured to cut and ablate a portion of septal wall tissue concurrently, e.g., via surfaces 936. For example, surfaces 936 may comprise an electrical conductor heated to an ablative temperature, or a plasma at an ablative temperature, that cuts via ablation, and limits the extent of ablation of septal wall tissue to the cut edges and/or very near the cut edges and biostabilizing the cut edges. In other examples, surfaces 936 may be sharp and at an ablative temperature and may be configured to both cut (e.g., mechanically) and ablate via the same surface 936 to cut and biostabilize the cut edges, and optionally tissue relatively near the cut edges.

Figure 11:
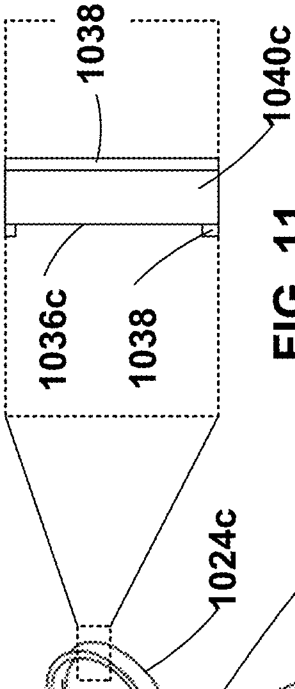
FIG. 11 is an enlarged perspective view depicting a portion of the cutting tool of FIG. 10.
Figure 10:
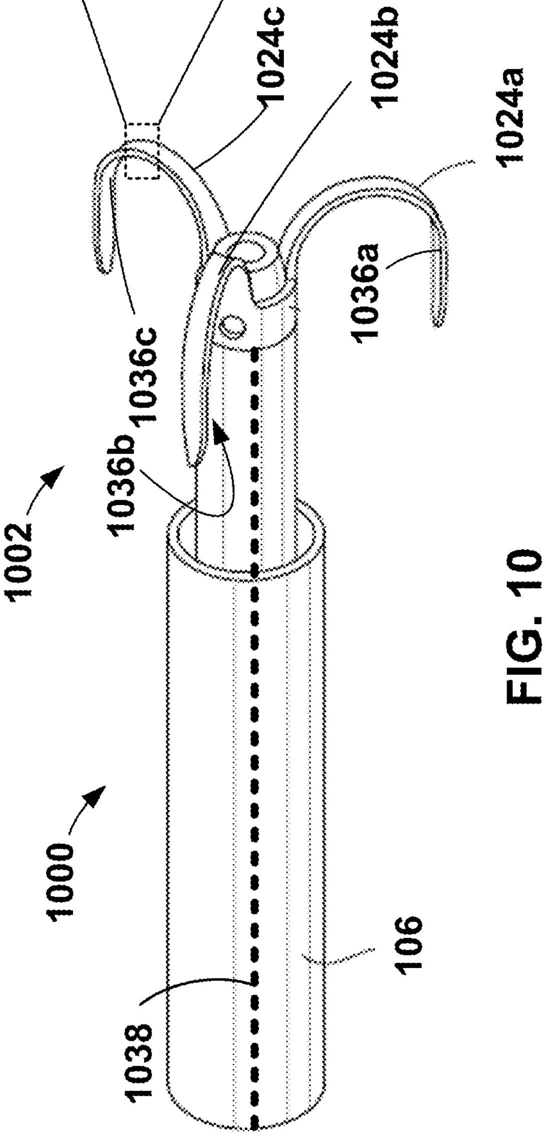
FIG. 10 is a perspective view depicting an example medical system, including a cutting tool.

FIG. 10 is a perspective view depicting an example medical system 1000, including a cutting tool 1002, and FIG. 11 is an enlarged perspective view depicting a portion of cutting tool 1002 of FIG. 10. Medical system 1000 may be substantially similar to medical system 700 described above, except that expandable members 1024 include surfaces 1036 substantially similar to surfaces 936 of FIG. 9, and energy source 1038 substantially similar to energy source 938 of FIG. 9. Expandable members 1024 may be substantially similar to expandable members 724 described above, except expandable members 1024 may be coated with, and/or encapsulated within, dielectric layer 1038 (including edge 1040*c* shown in FIG. 11) except for surfaces 1036.

Similar to as describe above, all conductive and/or metal components of cutting tool 1002 are coated with, and/or encapsulated within, dielectric layer 1038, e.g., a polymer, polytetrafluoroethylene (PTFE), parylene, or the like, except for surfaces 1036*a*, 1036*b*, and 1036*c*, collectively "surfaces 1036." In some examples, surfaces 1036 are configured to cut and ablate a portion of septal wall tissue concurrently. For example, surfaces 1036 may comprise an electrical conductor heated to an ablative temperature, or a plasma at an ablative temperature, that cuts via ablation, and limits the extent of ablation of septal wall tissue to the cut edges and/or very near the cut edges and biostabilizing the cut edges. In other examples, surfaces 1036 may be sharp and at an ablative temperature and may be configured to both cut (e.g., mechanically) and ablate via the same surfaces 1036 to cut and biostabilize the cut edges, and optionally tissue relatively near the cut edges.

Accordingly, although example systems and techniques have been shown and described, it is to be understood that all the terms used herein are descriptive rather than limiting, and that many changes, modifications, and substitutions may be made by one having ordinary skill in the art without departing from the spirit and scope of the invention. The following examples are examples of systems, devices, and methods described herein.

Example 1: A method including: cutting a septal wall between a right atrium and left atrium of a heart of a patient, wherein cutting the septal wall forms a multi-cuspid valvular shunt; and ablating septal wall tissue of at least a portion of the multi-cuspid valvular shunt, wherein the ablated tissue causes the at least a portion of the multi-cuspid valvular shunt to be biostable.

Example 2: The method of example 1, wherein cutting the septal wall and ablating septal wall tissue occur concurrently.

Example 3: The method of example 1 or 2, wherein ablating septal wall tissue comprises at least one of radiofrequency ablation, microwave ablation, or pulsed field ablation.

Example 4: The method of any one of examples 1 through 3, wherein plasma cutting elements form the multi-cuspid valvular shunt and ablates septal wall tissue.

Example 5: The method of any one of examples 1 through 4 wherein ablating septal wall tissue comprises ablating only septal wall tissue along the edges of the cut septal wall tissue.

Example 6: The method of any one of examples 1 through 5, further including: prior to cutting the septal wall, puncturing the septal wall with a cutting tool; extending a portion of the cutting tool through the septal wall from the right atrium to the left atrium or from the left atrium to the right atrium; and expanding a plurality of cutting members radially from the cutting tool, the plurality of cutting members disposed circumferentially around a longitudinal axis of the cutting tool at a plurality of circumferential positions, wherein cutting the septal wall comprises retracting the portion of the cutting tool through the septal wall with the cutting members expanded.

Example 7: The method of example 6, wherein ablating septal wall tissue occurs prior to puncturing the septal wall, wherein ablating septal wall tissue comprises ablating only an area of septal wall tissue corresponding to the circumferential positions of the plurality of cutting members and a radial extent of the plurality of cutting members.

Example 8: The method of example 6 or 7, wherein ablating septal wall tissue occurs after cutting the septal wall, wherein ablating septal wall tissue comprises cryoablating a portion of the septal wall including the cut septal wall tissue.

Example 9: A medical system including: a catheter defining a lumen; a first inner member configured to be received in the catheter lumen and extend distally outward from a distal opening of the catheter, wherein the inner member comprises: an elongated support member configured to move axially within the catheter lumen, the elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a cutting member configured to cut a septal wall tissue; and a second inner member configured to be received in the catheter lumen and extend distally outward from a distal opening of the catheter, wherein the first inner member is configured to form a multi-cuspid valvular shunt in the septal wall tissue, wherein the second inner member is configured to ablate at least a portion of the multi-cuspid valvular shunt such that the multi-cuspid valvular shunt is biostable.

Example 10: The medical system of example 9, wherein the first inner member and the second inner member are configured to form the multi-cuspid valvular shunt and ablate the at least a portion of the multi-cuspid valvular shunt concurrently.

Example 11: The medical system of example 9 or 10, wherein the cutting member of each of the plurality of expandable members comprises at least one of a plasma cutting element or a conductive element heated via radiofrequency heating.

Example 12: The medical system of any one of examples 9 through 11, wherein the cutting member of each of the plurality of expandable members comprises a blade.

Example 13: The medical system of any one of examples 9 through 12, wherein the second inner member is configured to deliver at least one of radiofrequency energy, microwave energy, or pulsed electric field energy to ablate the septal tissue.

Example 14: The medical system of example 13, wherein the second inner member is configured to ablate only an area of septal wall tissue corresponding to the circumferential positions of the plurality of expandable members and a radial extent of the plurality of expandable members.

Example 15: The medical system of any one of examples 9 through 14, wherein a distal end of each of the plurality of expandable members is attached to the elongated support member and a proximal end of each of the plurality of expandable members is attached to a movable member, wherein the movable member is configured to move axially towards and away from the distal end of the elongated support member to axially compress and extend each of the plurality of expandable members along the longitudinal axis, wherein the portion of each of the plurality of expandable members is configured to radially extend away from the elongated support member upon being compressed in the axial direction to a deployed configuration by the movable member and to radially retract towards the elongated support member upon being extended in the radial direction to a delivery configuration via the movable member.

Example 16: The medical system of example 15, wherein a proximal portion of each of the expandable members is configured to be at an angle with respect to the elongated support member when in the deployed configuration.

Example 17: The medical system of example 15 or 16, wherein the movable member comprises a threaded shaft, wherein the threaded shaft is configured to move in the axial direction upon being rotated.

Example 18: The medical system of any one of examples 15 through 17, further comprising at least one wire attached to the elongated support member and configured to proximally move the elongated support member relative to the movable member and to release the elongated support member to distally move away from the movable member.

Example 19: A medical device including: an elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a plasma cutting element configured to cut a septal wall tissue via plasma cutting to form a multi-cuspid valvular shunt in the septal wall tissue, wherein the plasma cutting element is configured to ablate only a portion of the multi-cuspid valvular shunt along the cut edges of the septal wall tissue such that the multi-cuspid valvular shunt is biostable.

Example 20: The medical device of example 19, wherein the plasma cutting element is configured to form the multi-cuspid valvular shunt and ablate the at least a portion of the multi-cuspid valvular shunt concurrently.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:

cutting a septal wall between a right atrium and left atrium of a heart of a patient, wherein cutting the septal wall forms a multi-cuspid valvular shunt; and ablating septal wall tissue of at least a portion of the multi-cuspid valvular shunt, wherein the ablated tissue causes the at least a portion of the multi-cuspid valvular shunt to be biostable.

2. The method of claim 1, wherein cutting the septal wall and ablating septal wall tissue occur concurrently.

3. The method of claim 1, wherein ablating septal wall tissue comprises at least one of radiofrequency ablation, microwave ablation, or pulsed field ablation.

4. The method of claim 1, wherein plasma cutting elements form the multi-cuspid valvular shunt and ablates septal wall tissue.

5. The method of claim 1 wherein ablating septal wall tissue comprises ablating only septal wall tissue along the edges of the cut septal wall tissue.

6. The method of claim 1, further comprising:

prior to cutting the septal wall, puncturing the septal wall with a cutting tool;

extending a portion of the cutting tool through the septal wall from the right atrium to the left atrium or from the left atrium to the right atrium; and expanding a plurality of cutting members radially from the cutting tool, the plurality of cutting members disposed circumferentially around a longitudinal axis of the cutting tool at a plurality of circumferential positions, wherein cutting the septal wall comprises retracting the portion of the cutting tool through the septal wall with the cutting members expanded.

7. The method of claim 6, wherein ablating septal wall tissue occurs prior to puncturing the septal wall, wherein ablating septal wall tissue comprises ablating only an area of septal wall tissue corresponding to the circumferential positions of the plurality of cutting members and a radial extent of the plurality of cutting members.

8. The method of claim 6, wherein ablating septal wall tissue occurs after cutting the septal wall, wherein ablating septal wall tissue comprises cryoablating a portion of the septal wall including the cut septal wall tissue.

9. A medical system comprising:

a catheter defining a lumen;

a first inner member configured to be received in the lumen of the catheter and extend distally outward from a distal opening of the catheter, wherein the first inner member comprises:

an elongated support member configured to move axially within the lumen of the catheter, the elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a cutting member configured to cut a septal wall tissue; and a second inner member configured to be received in the lumen of the catheter and extend distally outward from a distal opening of the catheter, wherein the first inner member is configured to form a multi-cuspid valvular shunt in the septal wall tissue, wherein the second inner member is configured to ablate at least a portion of the multi-cuspid valvular shunt such that the multi-cuspid valvular shunt is biostable.

10. The medical system of claim 9, wherein the first inner member and the second inner member are configured to form the multi-cuspid valvular shunt and ablate the at least a portion of the multi-cuspid valvular shunt concurrently.

11. The medical system of claim 9, wherein the cutting member of each of the plurality of expandable members comprises at least one of a plasma cutting element or a conductive element heated via radiofrequency heating.

12. The medical system of claim 9, wherein the cutting member of each of the plurality of expandable members comprises a blade.

13. The medical system of claim 9, wherein the second inner member is configured to deliver at least one of radiofrequency energy, microwave energy, or pulsed electric field energy to ablate the septal wall tissue.

14. The medical system of claim 13, wherein the second inner member is configured to ablate only an area of septal wall tissue corresponding to the circumferential positions of the plurality of expandable members and a radial extent of the plurality of expandable members.

15. The medical system of claim 9, wherein a distal end of each of the plurality of expandable members is attached to the elongated support member and a proximal end of each of the plurality of expandable members is attached to a movable member, wherein the movable member is configured to move axially towards and away from the distal end of the elongated support member to axially compress and extend each of the plurality of expandable members along the longitudinal axis, wherein the portion of each of the plurality of expandable members is configured to radially extend away from the elongated support member upon being compressed in an axial direction to a deployed configuration by the movable member and to radially retract towards the elongated support member upon being extended in a radial direction to a delivery configuration via the movable member.

16. The medical system of claim 15, wherein a proximal portion of each of the expandable members is configured to be at an angle with respect to the elongated support member when in the deployed configuration.

17. The medical system of claim 15, wherein the movable member comprises a threaded shaft, wherein the threaded shaft is configured to move in the axial direction upon being rotated.

18. The medical system of claim 15, further comprising at least one wire attached to the elongated support member and configured to proximally move the elongated support member relative to the movable member and to release the elongated support member to distally move away from the movable member.

19. A medical device comprising:

an elongated support member defining a longitudinal axis; and a plurality of expandable members at a distal portion of the elongated support member, wherein the plurality of expandable members are positioned circumferentially about the elongated support member, wherein at least a portion of each of the expandable members is configured to radially extend from the elongated support member, wherein each of the plurality of expandable members include a plasma cutting element configured to cut a septal wall tissue via plasma cutting to form a multi-cuspid valvular shunt in the septal wall tissue, wherein the plasma cutting element is configured to ablate only a portion of the multi-cuspid valvular shunt along cut edges of the septal wall tissue such that the multi-cuspid valvular shunt is biostable.

20. The medical device of claim 19, wherein the plasma cutting element is configured to form the multi-cuspid valvular shunt and ablate the at least a portion of the multi-cuspid valvular shunt concurrently.

* * * * *